(12) United States Patent
Fitch et al.

(10) Patent No.: US 8,560,277 B2
(45) Date of Patent: Oct. 15, 2013

(54) CREATING A LOAD BALANCED SPATIAL PARTITIONING OF A STRUCTURED, DIFFUSING SYSTEM OF PARTICLES

(75) Inventors: Blake G. Fitch, Croton-On-Hudson, NY (US); Robert S. Germain, Larchmont, NY (US); Michael C. Pitman, Wappingers Falls, NY (US); Aleksandr Rayshubskiy, New Rochelle, NY (US)

(73) Assignee: International Business Machines Corporation, Armonk, NY (US)

( * ) Notice: Subject to any disclaimer, the term of this patent is extended or adjusted under 35 U.S.C. 154(b) by 868 days.

(21) Appl. No.: 12/245,344

(22) Filed: Oct. 3, 2008

(65) Prior Publication Data
US 2010/0088080 A1   Apr. 8, 2010

(51) Int. Cl.
G06F 7/60 (2006.01)
G06F 17/10 (2006.01)
G06G 7/48 (2006.01)
G06G 7/58 (2006.01)

(52) U.S. Cl.
USPC ..................................... 703/2; 703/6; 703/11

(58) Field of Classification Search
USPC ............................................... 703/1, 6, 11, 2
See application file for complete search history.

(56) References Cited

U.S. PATENT DOCUMENTS

| 7,860,695 | B2 * | 12/2010 | Fitch et al. | 703/6 |
| 2006/0101104 | A1 * | 5/2006 | Bhanot et al. | 708/105 |
| 2006/0241928 | A1 | 10/2006 | Fitch et al. | |
| 2007/0233440 | A1 | 10/2007 | Fitch et al. | |
| 2008/0183435 | A1 | 7/2008 | Fitch et al. | |
| 2008/0189093 | A1 | 8/2008 | Fitch et al. | |
| 2008/0234990 | A1 * | 9/2008 | Bowers | 703/1 |
| 2008/0300839 | A1 | 12/2008 | Fitch et al. | |

FOREIGN PATENT DOCUMENTS

WO   WO2006115554   11/2006

OTHER PUBLICATIONS

Teresco et al., "Partitioning and Dynamic Load Balancing for the Numerical Solution of Partial Differential Equations," Numerical Solution of Partial Differential Equations on Parallel Computers, A.M. Bruaset, P. Bjørstad, and A. Tveito, eds., Springer-Verlag, 2005.*
Dove, M. T., and G. Stuart Pawley. "A molecular dynamics simulation study of the orientationally disordered phase of sulphur hexafluoride." Journal of Physics C: Solid State Physics 17.36 (2000): 6581.*
N. R. Adiga et al., "An Overview of the BlueGene/L Supercomputer," Proceedings of the ACM/IEEE Supercomputing 2002 Conference (SC'02), Nov. 2002, pp. 1-22.
F. Allen et al., "Blue Gene: A Vision for Protein Science Using a Petaflop Supercomputer," IBM Systems Journal, Mar. 2001, pp. 310-327, vol. 40, No. 2.

(Continued)

*Primary Examiner* — Mary C Jacob
*Assistant Examiner* — Aniss Chad
(74) *Attorney, Agent, or Firm* — Vazken Alexanian; Ryan, Mason & Lewis, LLP

(57) ABSTRACT

Techniques are disclosed for creating a load balanced spatial partitioning of a structured, diffusing system of particles. An exemplary method includes steps of determining a subset of a set of nodes within a given portion of the coordinate system intersected by a surface defined by points having a given distance from the surface of the given node; and mirroring the determined subset to at least another portion of the coordinate system.

15 Claims, 5 Drawing Sheets

(56) References Cited

OTHER PUBLICATIONS

B.G. Fitch et al., "Blue Matter: Approaching the Limits of Concurrency for Classical Molecular Dynamics," Proceedings of the ACM/IEEE Supercomputing 2006 Conference (SC'06), Nov. 2006, pp. 1-14.

L. Nyland et al., "Achieving Scalable Parallel Molecular Dynamics Using Dynamic Spatial Domain Decomposition Techniques," Journal of Parallel and Distributed Computing, Dec. 1997, pp. 125-138, vol. 47, No. 2.

A. Nakano, "Multiresolution Load Balancing in Curved Space: the Wavelet Representation," Concurrency: Practice and Experience, Jul. 1999, pp. 343-353, vol. 11, No. 7.

T.P. Straatsma et al., "Load Balancing of Molecular Dynamics Simulation with NWChem," IBM Systems Journal, Jun. 2001, pp. 328-341, vol. 40, No. 2.

B.G. Fitch et al., "Blue Matter, an Application Framework for Molecular Simulation on Blue Gene," Published in Journal of Parallel and Distributed Computing, IBM Research Report RC22683, May 2003, 41 pages, vol. 63.

* cited by examiner

CREATING A LOAD BALANCED SPATIAL PARTITIONING OF A STRUCTURED, DIFFUSING SYSTEM OF PARTICLES

CROSS-REFERENCE TO RELATED APPLICATIONS

This application is related to U.S. patent application Ser. No. 11/392,405 and U.S. patent application Ser. No. 11/113,939, the disclosures of which are incorporated by reference herein. These applications have the same inventive entity and assignee as the present application.

FIELD OF THE INVENTION

This invention generally relates to methods and systems for solving n-body problems, such as classical molecular dynamics. More specifically, the invention relates to methods and systems for creating a load balanced spatial partitioning of a structured, diffusing system of particles.

BACKGROUND OF THE INVENTION

Over the last few years, unprecedented computational resources have been developed, such as the BLUE GENE™ family of computers from the International Business Machines Corporation. See N. R. Adiga et al., "An Overview of the Blue Gene/L Supercomputer," Proceedings of the ACM/IEEE Supercomputing 2002 Conference (SC'02), November 2002, the disclosure of which is incorporated by reference herein. These resources may be used to attack, among other issues, grand challenge life sciences problems such as advancing the understanding of biologically important processes, in particular, the mechanisms behind protein folding.

In order to address this goal, attention has been directed to creating a classical molecular dynamics software package for long-time and large-scale molecular simulations. See F. Allen et al., "Blue Gene: A Vision for Protein Science Using a Petaflop Supercomputer," IBM Systems Journal, vol. 40, no. 2, pp. 310-327, 2001, the disclosure of which is incorporated by reference herein.

Classical molecular dynamics is predominantly an n-body problem. An n-body problem may be defined as the problem of finding, given the initial positions, masses, and velocities of n bodies, their subsequent motions as determined by classical mechanics. An n-body problem, for example molecular dynamics (MD), proceeds as a sequence of simulation time steps. At each time step, forces on particles, in MD atoms, are computed; and then the equations of motion are integrated to update the velocities and positions of the particles. In order to compute the forces on the particles, nominally the force between each particle and every other particle is computed, a computational burden of $O(n^2)$.

Practically speaking, molecular dynamics programs reduce the $O(n^2)$ by cutting off pair interactions at some distance. However for many scientifically relevant molecular systems, the computational burden due to the particle pair interactions remains large. In order to reach scientifically relevant simulation times, parallel computers are required to compute particle pair interactions rapidly. See B. G. Fitch et al., "Blue Matter: Approaching the Limits of Concurrency for Classical Molecular Dynamics," Proceedings of the ACM/IEEE SC 2006 Conference, Volume 11, Issue 17, November 2006, and B. G. Fitch et al., "Blue Matter, an Application Framework for Molecular Simulation on Blue Gene," Journal of Parallel and Distributed Computing, vol. 63, pp. 759-773, July 2003, the disclosures of which are incorporated by reference herein.

SUMMARY OF THE INVENTION

An illustrative embodiment of the invention provides a method of creating a load balanced spatial partitioning of a structured, diffusing system of particles. An exemplary method includes steps of determining a subset of a set of nodes within a given portion of the coordinate system intersected by a surface defined by points having a given distance from the surface of the given node; and mirroring the determined subset to at least another portion of the coordinate system.

Another illustrative embodiment of the invention includes an apparatus, comprising a memory and a processor coupled thereto, wherein the processor is operative to perform the steps of the method described above. Another illustrative embodiment of the invention includes a computer program product comprising a computer usable medium having computer usable program code embodied therewith. The computer usable program code comprising computer usable program code configured to perform the steps of the method described above.

Illustrative embodiments of the invention advantageously solve n-body problems such as classical molecular dynamics by geometrically mapping simulation space to a torus/mesh parallel computer's node space, thereby enabling the geometric n-body problem to be efficiently mapped to a machine with a fundamentally geometric processor space.

Illustrative embodiments of the invention create a load balanced spatial partitioning of a structured, diffusing system of particles with pairwise interactions that is scalable to a very large number of nodes and has favorable communications characteristics, including well defined bounds on the number of hops and the number of nodes to which a particle's position must be sent.

These and other objects, features, and advantages of the present invention will become apparent from the following detailed description of illustrative embodiments thereof, which is to be read in connection with the accompanying drawings.

DETAILED DESCRIPTION OF PREFERRED EMBODIMENTS

Figure 1:
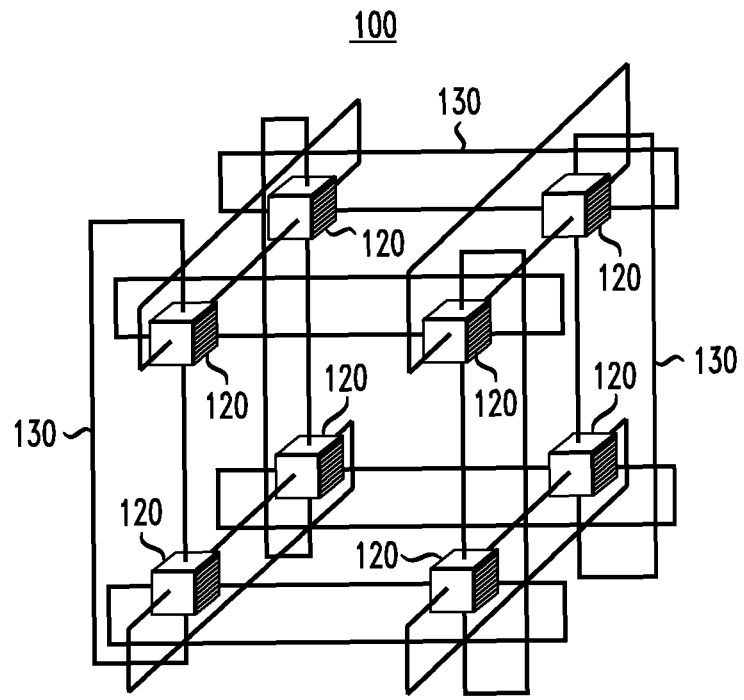
FIG. 1 illustrates a part of a torus computer system that may be used to practice this invention.

A preferred embodiment of the invention, described below in detail, provides a method and system for creating a load balanced spatial partitioning of a structured, diffusing system of particles with pairwise interactions that is scalable to a very large number of nodes and has favorable communications characteristics including well defined bounds on the number of hops and the number of nodes to which a particle's position must be sent.

Simulation space is divided up into equivalent volume elements. Node pair interactions, which are interactions between the particles in a pair of nodes, are assigned to one of the set of nodes defined by the intersection surfaces of the node pair; it should be noted that this set of nodes may be quite large.

Because pair interactions are cut-off beyond a defined radius $R_c$, an "interaction surface" can be described by a group of nodes containing a portion of the surface of a suitable specified convex shape that contains the sphere of radius $R_b = R_c/2$ centered about a simulation volume element. Such a convex shape may be a surface similar in shape to the volume element itself, with rounded corners. Since the interaction surface has a radius of $R_b$ around the volume element, it also contains the space having a radius of $R_b$ around each particle within the volume element. Accordingly, interactions between nodes may be managed rather than interactions between particles.

Accordingly, illustrative embodiments in accordance with inventive principles provide a technique for eliminating imbalances caused by local fluctuations in interaction workload, this allowing productive use of more nodes than there are particles in the system. Such a technique may allow for increased efficiency in solving n-body problems, such as those frequently encountered in molecular dynamics. This increased efficiency may be achieved by, for example, balancing the load associated with particle interaction computations across computational elements of the computer used to perform the simulation.

Although described primarily in terms of solving n-body problems on mesh/torus machines, any suitable computer or computer system may be used to implement the invention. In a preferred embodiment, the above-mentioned BLUE GENE™ family of computers may be used. The BLUE GENE™/L parallel computational platform does interprocessor communication primarily using a 3D torus network. Processor space is defined by the location of processors on the 3D torus network and communication costs between processors increase with distance. The methods described herein enable the geometric n-body problem to be efficiently mapped to a machine with a fundamentally geometric processor space, however these methods may also be applied to other network topologies.

In the discussion herein, the following definitions/conventions are used:

The term "node" refers to the computational element that forms nodes in the graph defined by the interconnection network. Any "node" may include one or more processors. Any suitable processing unit or units may be used in the node, and it is not necessary to describe the detail of the processing units.

The term "simulation space" refers to the domain of the n-body simulation.

The term "node space" refers to the geometry of the interconnections between nodes of the machine. Typically the discussion herein refers to a machine with a three-dimensional torus/mesh interconnect geometry in which each node is connected to its six nearest neighbors and is addressed by a triple of integers that represent its coordinates within the network. In a torus, periodic boundary conditions are implemented physically by connecting the nodes on opposite "faces" of the machine.

FIG. 1 illustrates a part of a computer system or structure that may be used in the implementation of the present invention. More specifically, FIG. 1 shows a part of a Massively Parallel Supercomputer architecture in the form of a three-dimensional torus designed to deliver processing power on the order of teraOPS (trillion floating-point operations per second) for a wide range of applications. The Massively Parallel supercomputer architecture, in an exemplary embodiment, may comprise 65,536 processing nodes organized as a 64×32×32 three-dimensional torus with each processing node connected to six (6) neighboring nodes.

In particular, FIG. 1 shows a torus comprised of eight nodes 120 connected together by links or connections 130. It is clear to see how this interconnect scales by increasing the number of nodes 120 along all three dimensions. With current technology, this architecture can be leveraged to hundreds of teraOPS. As will be understood by those of ordinary skill in the art, other computer structures may also be used in the practice of this invention.

Figure 2:
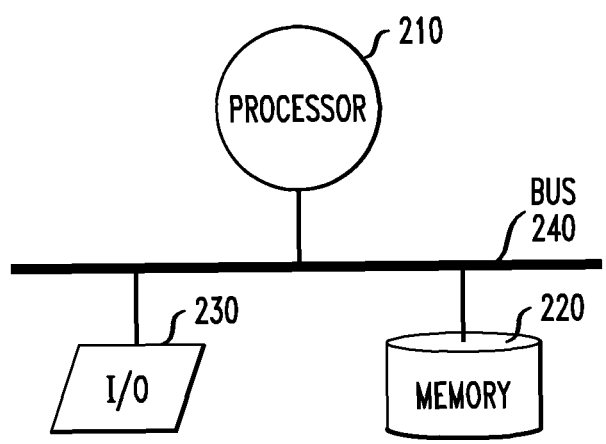
FIG. 2 is a block diagram depicting an exemplary processing system in which inventive techniques may be implemented.

FIG. 2 is a block diagram depicting an exemplary processing system 200 formed in accordance with an aspect of the invention. System 200 may represent the entire processing facility for use by the invention or a part thereof. System 200 may include a processor 210, memory 220 coupled to the processor (e.g., via a bus 240 or alternative connection means), as well as input/output (I/O) circuitry 230 operative to interface with the processor. The processor 210 may be configured to perform at least a portion of the methodologies of the present invention, illustrative embodiments of which are shown in the figures and described herein.

It is to be appreciated that the term "processor" as used herein is intended to include any processing device, such as, for example, one that includes a central processing unit (CPU) and/or other processing circuitry (e.g., digital signal processor (DSP), microprocessor, etc.). Additionally, it is to be understood that the term "processor" may refer to more than one processing device, and that various elements associated with a processing device may be shared by other processing devices. The term "memory" as used herein is intended to include memory and other computer-readable media associated with a processor or CPU, such as, for example, random access memory (RAM), read only memory (ROM), fixed storage media (e.g., a hard drive), removable storage media (e.g., a diskette), flash memory, etc.

Furthermore, the term "I/O circuitry" as used herein is intended to include, for example, one or more input devices (e.g., keyboard, mouse, etc.) for entering data to the processor, and/or one or more output devices (e.g., printer, monitor, etc.) for presenting the results associated with the processor. I/O circuitry 630 may comprise, for example, one or more ports operative to receive and/or transmit one or more data packets and/or one or more control messages.

Accordingly, an application program, or software components thereof, including instructions or code for performing the methodologies of the invention, as described herein, may be stored in one or more of the associated storage media (e.g., ROM, fixed or removable storage) and, when ready to be utilized, loaded in whole or in part (e.g., into RAM) and executed by the processor 210. In any case, it is to be appreciated that at least a portion of the components shown in the above figures may be implemented in various forms of hardware, software, or combinations thereof, e.g., one or more DSPs with associated memory, application-specific integrated circuit(s), functional circuitry, one or more operatively programmed general purpose digital computers with associated memory, etc. Given the teachings of the invention provided herein, one of ordinary skill in the art will be able to contemplate other implementations of the components of the invention.

A preferred embodiment in accordance with illustrative principles of the invention efficiently solves the n-body problem by geometrically mapping simulation space to a torus/mesh parallel computer's node space via a spatial decomposition. In a preferred embodiment, the mechanism for distributing the work is a broadcast of particle positions followed possibly by a reduction of forces on each particle to the node that broadcasted that particle (the home node).

A basic requirement of this method is the ability to broadcast data from one node to a subset of all the nodes in the system. The required collective operations can be constructed using point-to-point communications however; hardware may offer features to enhance the performance of these primitives such as multi-cast.

In a preferred mapping of simulation space to node space, simulation space is divided into the same number of subvolumes as there are nodes, and further, the simulation space preferably has the same extents (measured in voxels) in each dimension as node space (measured in nodes).

A sparse surface set is a set of nodes chosen from the set of nodes intersected by the "interaction surface" described above. Each node on each time step will broadcast to its sparse surface set, compute forces, then sum-reduce the force values on each particle. More specifically, two reciprocal communications operations are of interest:

Sparse surface set broadcast: given a convex shape in simulation space, broadcast data from the node containing the center of such a shape to a set of nodes intersecting a portion of the surface of that shape.

Sparse surface set reduce: given a convex shape in simulation space, theta-reduce data from a set of nodes intersecting a portion of the surface of that shape to the root node containing the center of the shape.

N-Body Spatial Decomposition for Load Balance

N-body problems in a periodic simulation space nominally have a computational burden defined by the order $O(N^2)$ pairwise particle interactions possible. In many applications, this computational burden is reduced to $O(N)$ by cutting off interactions between particles separated by more than a specified distance in periodic simulation space.

A natural way to map a spatial problem on a spatial connected machine is with a direct mapping, where the simulation space is uniformly assigned to processor space. For n-body systems (assuming that all pair interactions have the same computational cost) with a uniform density of particles or where no cut-offs are imposed, this simple mapping will result in a balanced load across the machine since each node or region of nodes will have roughly the same interaction computation workload.

However, a direct mapping may result in load imbalance. Load imbalance may be caused by uneven distribution of particles or differences in the types of load, such as those based on particle type or distance between interacting particles. There are several schemes for load balancing which may utilized in conjunction with embodiments of the present invention. Examples of such schemes may be found in, for example, U.S. patent application Ser. No. 11/392,405 and U.S. patent application Ser. No. 11/113,939, the disclosures of which are incorporated by reference herein.

Preferred Load Balancing Algorithm

Figure 3:
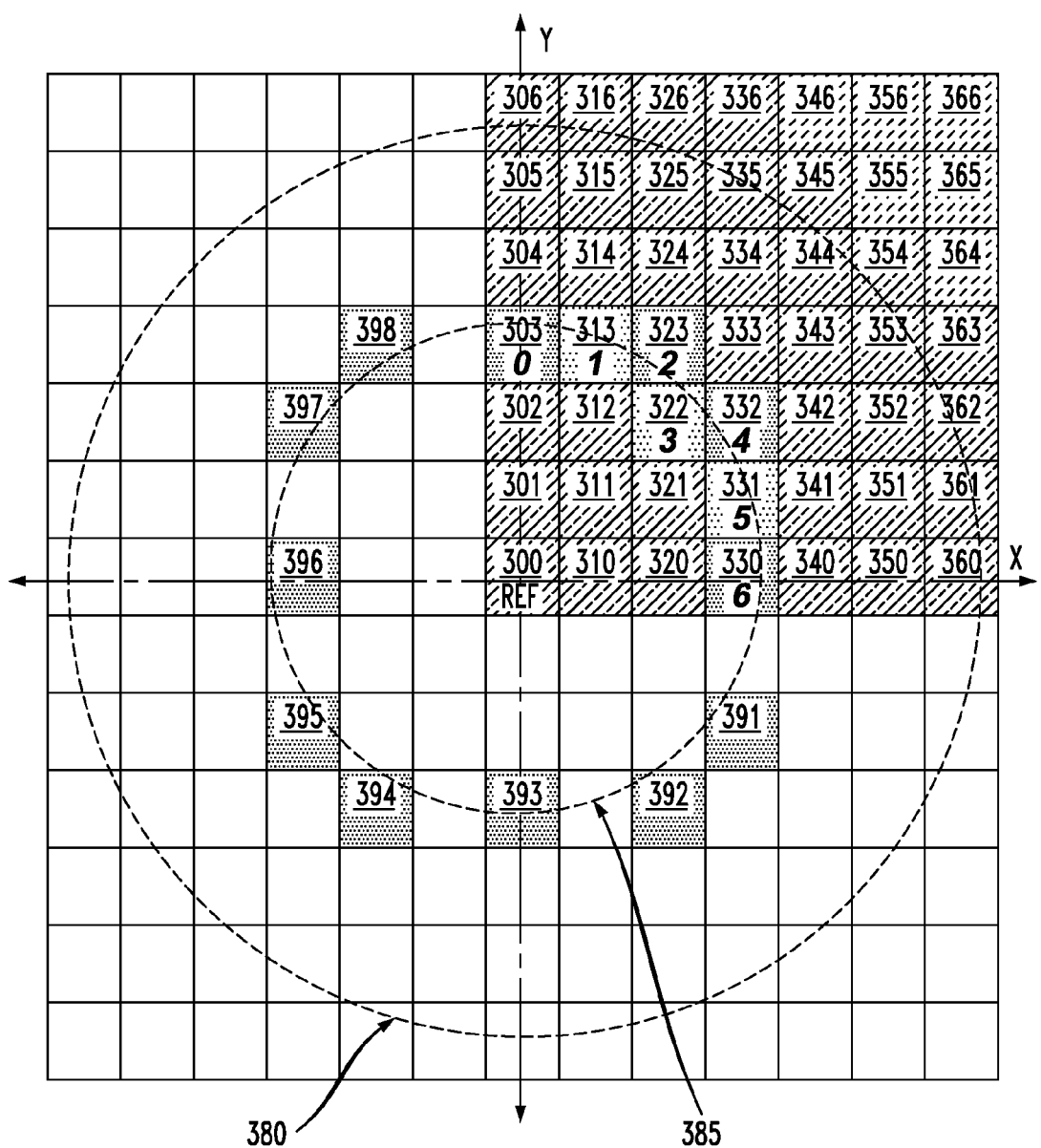
FIG. 3 shows a coordinate system with which an exemplary load balancing technique may be used.
Figure 4:
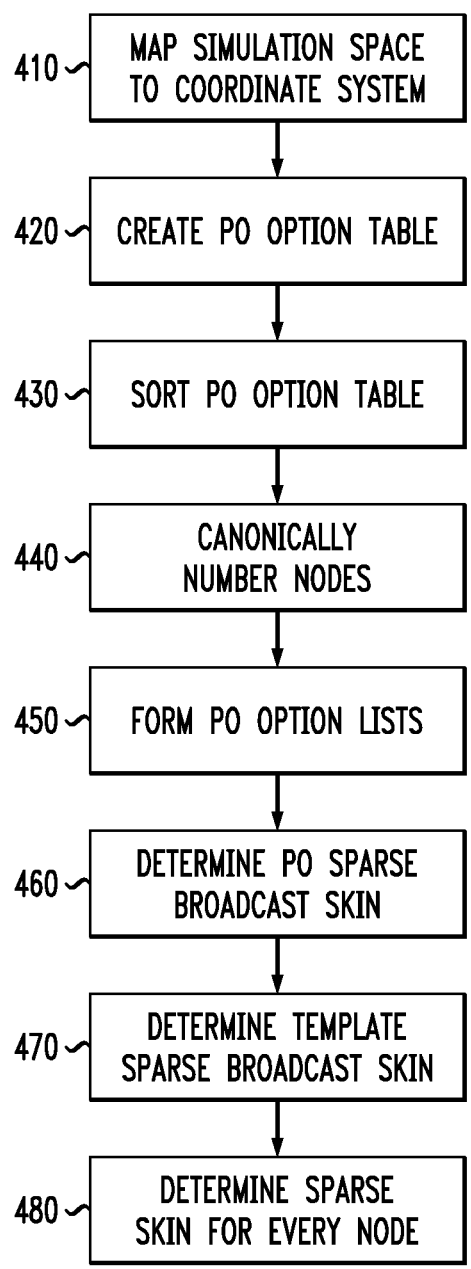
FIG. 4 is a flowchart showing an exemplary load balancing technique.

A preferred load balancing method suitable for use with illustrative embodiments of the present invention is described herein with reference to the coordinate system shown in FIG. 3 and the flowchart shown in FIG. 4. The load balancing method described herein is suitable for use with, for example, n-body problems such as those associated with molecular dynamics.

FIG. 3 shows a portion of a three-dimensional relative coordinate system defined on a lattice of nodes. This coordinate system has its origin on Reference Node 300, which has x-y-z coordinates <0, 0, 0>. This coordinate system will be used to illustrate certain definitions and conventions to be used in describing the method.

The coordinate system includes a Positive Octant (PO), defined herein as the set of nodes having non-negative displacements from the origin (e.g., Reference Node 300) in all three dimensions. The portion of the coordinate system shown in FIG. 3 includes 49 nodes within the PO: nodes 300-306, which have coordinates ranging from <0, 0, 0> to <0, 6, 0>; nodes 310-316, which have coordinates ranging from <1, 0, 0> to <1, 6, 0>; nodes 320-326, which have coordinates ranging from <2, 0, 0> to <2, 6, 0>; nodes 330-336, which have coordinates ranging from <3, 0, 0> to <3, 6, 0>; nodes 340-346, which have coordinates ranging from <4, 0, 0> to <4, 6, 0>; nodes 350-356, which have coordinates ranging from <5, 0, 0> to <5, 6, 0>; and nodes 360-366, which have x-y-z coordinates ranging from <6, 0, 0> to <6, 6, 0>.

A given node having coordinates <x, y, z> may be considered one of a set of up to eight "mirror nodes," which are defined as the nodes having coordinates <±x, ±y, ±z>. It should be noted that a set of mirror nodes will typically include only one node within each octant. Moreover, this set of mirror nodes will include a node within each octant, unless one or more of the x-y-z coordinates is zero. For example, node 323, which has coordinates of <2, 3, 0>, has mirror nodes including node 392, which has coordinates of <2, −3, 0>; node 394, which has coordinates of <−2, −3, 0>; and node 398, which has coordinates of <−2, 3, 0>. Node 303, which has coordinates of <0, 3, 0>, has only one mirror node shown in FIG. 3; namely, node 393, which has coordinates of <0, −3, 0>. It should be noted that finding the mirror within the Positive Octant (or PO mirror) for a given node merely requires taking the absolute value of each coordinate. For example, the PO mirror of a node with coordinates of <−13, 4, −2> is <13, 4, 2>.

It should noticed that although the illustrative embodiment described herein is implemented using a three-dimensional coordinate system, other coordinate systems may be used in conjunction with illustrative embodiments of the invention. For example, an illustrative embodiment may be implemented using a two-dimensional coordinate system, in which the positive octant may be replaced by the positive quadrant. Likewise, other portions of the coordinate systems may be used instead of the positive octant and/or positive quadrant included, but not limited to, other octants and/or quadrants within the coordinate system.

The Effective Cutoff, or Rc, is a specified distance from a given node beyond which pair interactions are cut off.

A Node Interaction Set is defined as the set of nodes which map to (or contain) any simulation space within Effective Cutoff of a given node, typically the Reference Node. This set may be thought of as comprising the nodes interacting with those of the Reference Node.

PO-nodes refer to those nodes within both the Node Interaction Set and the Positive Octant. In the coordinate system shown in FIG. 3, sphere 380 has a radius equal to the Effective Cutoff. The PO-nodes shown in FIG. 3 include nodes 300 to 306, 310 to 316, 320 to 326, 330 to 336, 340 to 345, 350 to 354 and 360 to 363. At least a portion of each of these nodes is contained within sphere 380. The Node Interaction Set shown in FIG. 3 includes the PO-nodes as well as the mirrors of the PO-nodes, such as nodes 391-398.

A Full Broadcast Skin includes all those nodes intersected by a surface defined by all points having a distance of one-half of the Effective Cutoff from the surface of the Reference-Node. In other words, the Full Broadcast-Skin is the set of nodes containing some portion of the locus of points exactly one-half of the Effective Cutoff from the surface of the reference nodes. The PO Full Broadcast Skin are the nodes on the Full Broadcast Skin of the Reference Node in the Positive Octant.

In the coordinate system shown in FIG. 3, sphere 385 has a radius equal to one-half of the Effective Cutoff (i.e., one-half of the radius of sphere 380). Thus, the Full Broadcast Skin includes those nodes through which sphere 385 passes. The Full Broadcast Skin includes the PO Full Broadcast Skin, which includes nodes 303, 313, 323, 322, 332, 331 and 330, as well as the mirrors thereof, such as nodes 391-398.

A Template Sparse Broadcast-Skin is defined as the set of nodes which the Reference-Node must send particle positions to such that if every other node sent particles to an equivalent relative Sparse Skin Set, every pair of particles within cutoff of the Reference-Node would be realize on at least one Sparse Broadcast-Skin node. A PO Sparse Broadcast-Skin comprises those nodes in the Template Sparse Broadcast-Skin set and the Positive Octant. As will be discussed hereafter, the method will first develop a PO Sparse Broadcast-Skin which then, based on 3D symmetry, will be mirrored to create a Template Sparse Broadcast-Skin.

Turning now to the flowchart shown in FIG. 4, the method begins in step 410 with the assignment of volume elements to nodes such there is a one-to-one correspondence between nodes and volume elements in the simulation elements. This preferably is a "natural" mapping in which the simulation space is divided into equally sized volume elements that map simulation space onto node space in a way similar to that which would be obtained via the ORB technique if load were uniformly distributed throughout the simulation volume.

In step 420, a PO option table for the Reference-Node is created with an entry for every PO node. Each entry within this PO option table is a PO option list is created by taking each node in the intersection of the Reference-Node's Broadcast Skin and the PO node's Broadcast Skin, finding that node's mirror in the Positive Octant and making an entry if that mirror node has not already been added.

In step 430, the PO option table is sorted by PO option list size in descending order.

In step 440, the nodes on the Reference-Node's PO Broadcast Skin are canonically numbered so that these numbers may be used to identify bit fields in a compressed representation of a PO Sparse Broadcast Skin as selected nodes on that PO Broadcast Skin. In the example shown in FIG. 3, the Reference-Node's PO Broadcast Skin comprises nodes 303, 313, 323, 322, 332, 331 and 330, which have canonically numbered as "0" through "6," respectively. One having skill in the art will understand that other techniques may be used to scan representations of sparse skins in addition to or instead of this bit array technique.

In step 450, a PO option list is formed for each for each PO option table entry. This PO Option list is defined as a Binary PO Option List which is a bit field with 0 for bits representing nodes not in the list and 1 for nodes that are on the list based on the canonical numbering of step 440, where the canonical cell number gives the bit position in the bit field. This is the Binary PO Option Table.

In the example shown in FIG. 3, this Binary PO Option List is 1010101. This bit field has a "1" in the 0th, 2nd, 4th and 6th positions, and a "0" in the 1st, 3rd, and 5th positions. This indicates that, of the nodes canonically numbered "0" to "6," the nodes numbered as "0," "2," "4," and "6" are in the list and the nodes numbered as "1," "3," and "5" are not in the list.

In step 460, a search is performed of the smallest set of reference node PO Broadcast Skin nodes which have at least one node intersection in every PO Option table entry. Because the lists in this table will be subsets of the full broadcast skins defined by the geometries of the simulation and node spaces, the result of this process is referred to as the PO sparse skin table.

This is a systematic search, and it may be parallelized by dividing the search space across parallel nodes. Starting with the number of nodes that is the minimum estimated to satisfy the condition of having at least one node that intersects every PO Option table entry, iterate through all combinations of PO Broadcast Nodes. For example, if there are 32 nodes in the Reference-Node PO Broadcast Skin and five nodes are estimated to be the minimum, begin scanning 32-choose-5. Each bit pattern is a Candidate PO Sparse skin solution and is a scan value. For each scan value, loop over the Binary PO Option Table matching Binary PO Option Lists.

Many variants of this scheme outlined are possible including the inclusion of a weighting field in the option table that could be computed, for example, from the actual count of particle pairs within range for each pair of nodes/volume elements. Algorithms applicable to the "bin-packing" problem could be adapted for use in this load-balancing problem.

In an illustrative embodiment, the scan value fails if binary ANDing the scan value with any Binary PO Option list results in 0 (zero). A zero the PO Broadcast Skin pattern does not satisfy all the interaction requirements. Because we sorted the PO Option Table according to occupancy of PO Option Lists, the first checks will be of the most constrained node pairs, thereby saving work. The scan succeeds if a scan value can be ANDed with each Binary PO Option List with a non-zero result—this is a candidate solution.

More than one candidate solution may occur when scanning for a certain number of nodes in the Candidate PO Sparse skin solution. One may select the first successful candidate or keep scanning for other candidates that may have better distributions to minimize communication costs. A possible criterion for selecting among multiple solutions may be defined in terms of more detailed network routing costs given the specific distribution of the solution.

In step 470, once a candidate is chosen, the candidate PO Sparse Skin is used to create a Template Sparse Broadcast Skin (the sparse skin for the reference node) by mirroring the candidate into each of the 7 other octants. As discussed above, the mirroring operation produces at most 7 additional coordinates from the original coordinate <x, y, z> in the PO by generating all permutations of <±x, ±y, ±z>. This is the group of all mirrors in three dimensions.

In step 480, the Template Sparse Broadcast Skin is used to generate the sparse skin for every node in the simulation by considering each simulation node as the Reference-Node and the solution set nodes as relative displacements from the Reference-Node.

Molecular Dynamics Decompositions Based on Ellipsoidal Communications Primitives Optimal Interaction Assignment Using Dynamic Interaction Balancing Molecular dynamics as applied to biomolecular simulation of fixed sized problems on very large, geometric node spaces requires a simulation space to node space mapping that, preferably, maintains as much locality as possible while balancing workload. This is so communication costs and computational costs are minimized in balance.

To do this, the minimal set of communicating nodes for a particular particle must be identified; for example, using the method described above with reference to FIGS. 3 and 4. The minimal set of communicating nodes is defined as all those nodes which contain any of the surface of a specified convex volume containing the spherical volume of space (with radius greater than half the cutoff radius) centered about the particle. This defines a minimal volume in node space that ensures that there exists at least one node for every pair of particles within cutoff that can calculate the interaction between that pair.

During each simulation step, each node sends all its particle positions to each of its communication partners and receives from each a set of particle positions. A node may be assigned to evaluate the interaction between any pair of particles in the set of positions it has received.

Figure 5:
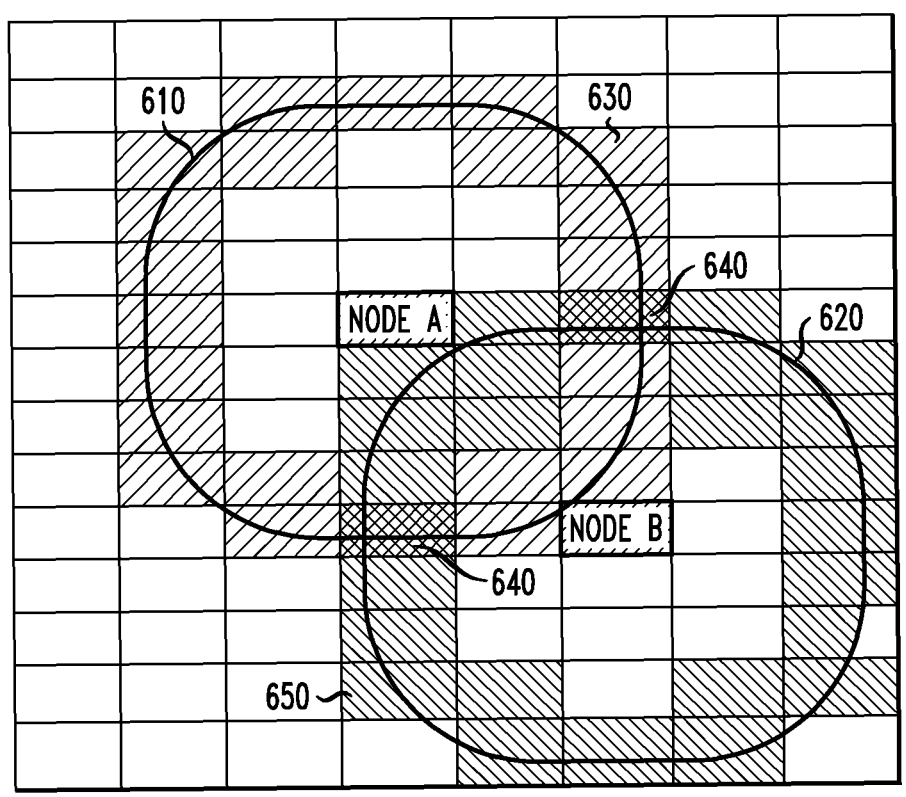
FIG. 5 shows broadcast zones for two nodes.

Although pairs of particle positions in the simulation space separated by close to the cutoff distance might be received by only a single node creating a definitive assignment, generally the positions of any given pair of particles will be received by several nodes as shown in FIG. 5, any one of which may be assigned that pair's interaction.

FIG. 5 shows the broadcast zones 610 and 620 for two nodes superimposed on the spatial decomposition of the domain onto all nodes (two-dimensional view for simplicity). The nodes that contain portions of the surface in simulation space defined by the surface of the volume defined by the set of points within radius $R_b$ of any voxel assigned to Node A are shown in one type of hatching 630 with a different hatching 640 where the nodes also contain portions of the surface in simulation space defined by the surface of the volume defined by the set of points within Rb of any voxel assigned to Node B (which are marked with one type of hatching 650 except where overlap occurs). The broadcast radius $R_b > R_c/2$ where $R_c$ is the cutoff radius. The interaction between a particle stored on Node A and a particle stored on Node B can be computed on any of the nodes with cross-hatching.

Interaction assignment may be accomplished by any method, which results in the interaction between a pair of particles being done once on one node. An example of a suitable algorithm is to specify that the interaction will be done on the node that has received both particle positions and has the minimum node id number. Such algorithms however have load balancing characteristics which reflect the spatial mapping technique used.

In order to reduce micro load imbalance, dynamic deterministic interaction assignment can be employed. These techniques allow rapid overlapping regional averaging. To enable these techniques, each node must measure its current computational load and add this value to each message it sends to its communication partners. When a node receives its set of [load, position set] messages from its communicating partners, it now has enough information to deterministically assign itself a set of interactions. The set of interactions each node can contribute to load averaging among its communication partners.

An example of an algorithm, illustrated in FIG. 6, which allows deterministic, averaged interaction assignment is as follows:

At step 710, receive a complete set of [load, position set] messages from communicating partners. At step 720, for each pair of received messages, create a canonical interaction list including the effects of range cutoffs. At step 730, for each pair of messages received, determine the set of nodes that also received this pair of messages. At step 740, using a deterministic algorithm, assign each interaction (appearing on the canonical interaction list) that could be computed by the above set of nodes to one of those nodes.

In an illustrative embodiment, assignment could be done on a node basis as a bin-packing optimization problem to achieve good load balance. For each pair of nodes, the interaction for the particles contained within that pair is assigned to a node in the intersection of the Sparse Broadcast Skin sets.

Other examples of deterministic algorithms which may be used include:
- Using the loads reported on each of those nodes, assign interactions (which have been ordered in some canonical way) to attempt to equalize the new loads on each of the nodes.
- Randomizing the assignment of interactions to the node set using a hashing algorithm.
- Assigning each interaction to the node owning the voxel that contains the mid-point of the line connecting the interacting pair of particles.

Figure 6:
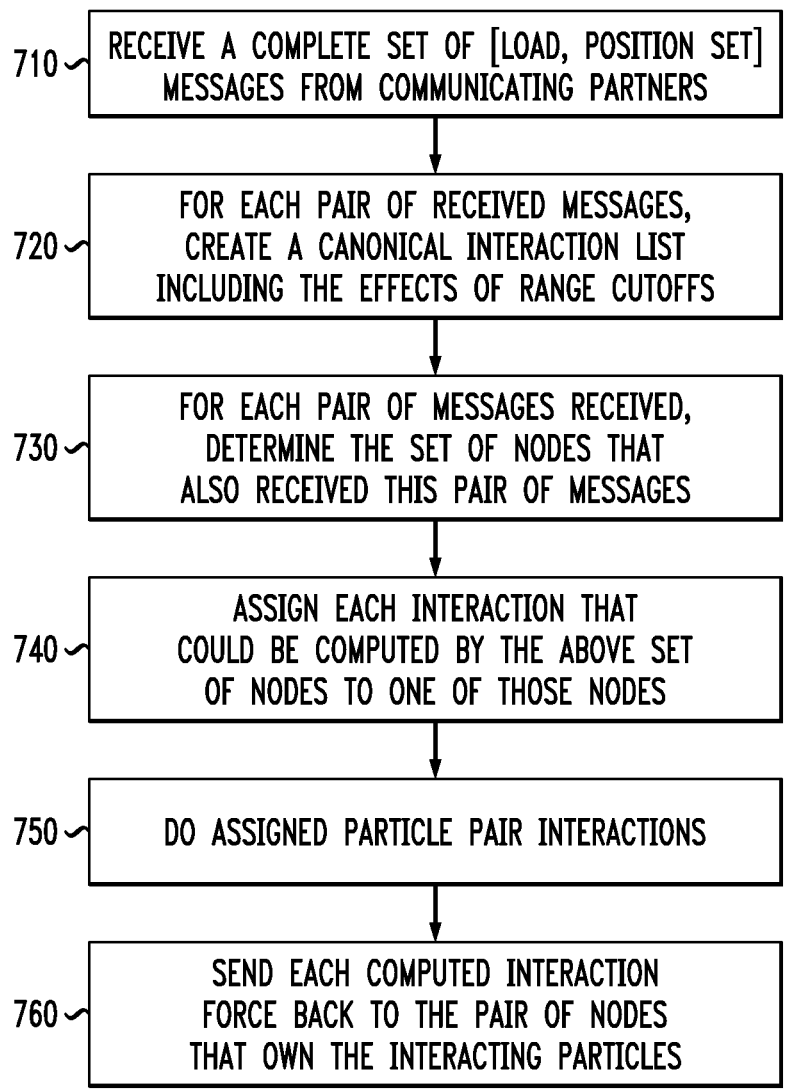
FIG. 6 shows an example of an algorithm that allows deterministic, averaged interaction assignment.

At step 750 of FIG. 6, do assigned particle pair interactions. At step 760, send each computed interaction force back to the pair of nodes that own the interacting particles.

Importantly, this algorithm costs only interaction computation. The cost of returning the force should be added to reflect lower communication cost of computing an interaction on a node which owns one of the particles.

For the purposes of increased scope for load balancing or in cases where communication costs are high relative to computation costs, it may be advantageous to increase the simulation space radius determining the communication partner set beyond $R_c/2$ to increase the number of nodes available for load balancing.

As heretofore noted, the present invention can be realized in hardware, software, or a combination of hardware and software. Any kind of computer/server system(s)—or other apparatus adapted for carrying out the methods described herein—is suited. A typical combination of hardware and software could be a general purpose computer system with a computer program that, when loaded and executed, carries out the respective methods described herein. Alternatively, a specific use computer, containing specialized hardware for carrying out one or more of the functional tasks of the invention, could be utilized.

The present invention, or aspects thereof, can also be embedded in a computer program product, which comprises all the respective features enabling the implementation of the methods described herein, and which—when loaded in a computer system—is able to carry out these methods. Computer program, software program, program, or software, in the present context mean any expression, in any language, code or notation, of a set of instructions intended to cause a system having an information processing capability to perform a particular function either directly or after either or both of the following: (a) conversion to another language, code or notation; and/or (b) reproduction in a different material form.

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

What is claimed is:
1. A method, comprising the steps of:
   determining a subset of a set of nodes within a given portion of a coordinate system intersected by a surface defined by points having a given distance from the surface of a given node, wherein each node comprises a plurality of particles and wherein the given node comprises an origin point of the coordinate system; and
   mirroring the determined subset of nodes to at least another portion of the coordinate system, wherein mirroring comprises mirroring each node in the determined subset of nodes, which has a given coordinate in a given octant, to a corresponding coordinate in at least one other octant of the coordinate system, wherein the determining and mirroring steps are repeated for each of a plurality of nodes within the coordinate system to create a load balanced spatial partitioning of a structured, diffusing system of particles with node pair interactions that comprise interactions between particles in a pair of nodes.

2. The method of claim 1, wherein the given portion of the coordinate system is a quadrant of a two-dimensional coordinate system.

3. The method of claim 1, wherein the given portion of the coordinate system is an octant of a three-dimensional coordinate system.

4. The method of claim 1, wherein the given distance is one half of an effective cutoff distance.

5. The method of claim 1, wherein the nodes within the coordinate system correspond to equally sized volume elements.

6. The method of claim 1, wherein the step of determining a subset of nodes further comprises the step of:

creating an option table comprising a set of entries representing respective nodes within an intersection of the set of nodes and a set of nodes within the given portion of the coordinate system intersected by a surface defined by points having the given distance from the surface of another node within the given portion of the coordinate system.

7. The method of claim 6, wherein the subset of nodes comprises a minimal set of nodes within the subset of nodes each having at least one node intersection in each option table entry.

8. An apparatus, comprising:

at least one memory; and at least one processor coupled to the memory, the processor being operative to perform the steps of:

determining a subset of a set of nodes within a given portion of a coordinate system intersected by a surface defined by points having a given distance from the surface of a given node, wherein each node comprises a plurality of particles and wherein the given node comprises an origin point of the coordinate system; and mirroring the determined subset of nodes to at least another portion of the coordinate system, wherein mirroring comprises mirroring each node in the determined subset of nodes, which has a given coordinate in a given octant, to a corresponding coordinate in at least one other octant of the coordinate system, wherein the determining and mirroring are repeated for each of a plurality of nodes within the coordinate system to create a load balanced spatial partitioning of a structured, diffusing system of particles with node pair interactions that comprise interactions between particles in a pair of nodes.

9. The apparatus of claim 8, wherein the given distance is one half an effective cutoff distance.

10. The apparatus of claim 8, wherein the step of determining a subset of nodes further comprises the step of:

creating an option table comprising a set of entries representing respective nodes within an intersection of the set of nodes and a set of nodes within the given portion of the coordinate system intersected by a surface defined by points having the given distance from the surface of another node within the given portion of the coordinate system.

11. The apparatus of claim 10, wherein the subset of nodes comprises a minimal set of nodes within the subset of nodes each having at least one node intersection in each option table entry.

12. A computer program product comprising a non-transitory computer readable storage medium having computer usable program code tangibly embodied therewith, wherein when executed by a computer, the computer usable program code is configured to perform the steps of:

determining a subset of a set of nodes within a given portion of a coordinate system intersected by a surface defined by points having a given distance from the surface of a given node, wherein each node comprises a plurality of particles and wherein the given node comprises an origin point of the coordinate system; and mirroring the determined subset of nodes to at least another portion of the coordinate system, wherein mirroring comprises mirroring each node in the determined subset of nodes, which has a given coordinate in a given octant, to a corresponding coordinate in at least one other octant of the coordinate system, wherein the determining and mirroring are repeated for each of a plurality of nodes within the coordinate system to create a load balanced spatial partitioning of a structured, diffusing system of particles with node pair interactions that comprise interactions between particles in a pair of nodes.

13. The computer program product of claim 12, wherein the given distance is one half of an effective cutoff distance.

14. The computer program product of claim 12, wherein the step of determining a subset of nodes further comprises the step of:

creating an option table comprising a set of entries representing respective nodes within an intersection of the set of nodes and a set of nodes within the given portion of the coordinate system intersected by a surface defined by points having the given distance from the surface of another node within the given portion of the coordinate system.

15. The computer program product of claim 14, wherein the subset of nodes comprises a minimal set of nodes within the subset of nodes each having at least one node intersection in each option table entry.

\* \* \* \* \*